United States Patent
Ogawa

(10) Patent No.: US 6,494,836 B2
(45) Date of Patent: Dec. 17, 2002

(54) METHOD OF GENERATING IMAGE DATA AND ULTRASONIC DIAGNOSTIC APPARATUS USING THE SAME

(75) Inventor: Eiji Ogawa, Minami-Ashigara (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 39 days.

(21) Appl. No.: 09/848,326

(22) Filed: May 4, 2001

(65) Prior Publication Data

US 2001/0044582 A1 Nov. 22, 2001

(30) Foreign Application Priority Data

May 15, 2000 (JP) ........................................ 2000-141283

(51) Int. Cl.⁷ ................................................ A61B 8/00
(52) U.S. Cl. ..................................... 600/443; 128/916
(58) Field of Search ................................ 600/437, 407, 600/438, 425, 440–447, 449–472, 586; 73/625, 626; 367/7, 11, 138; 128/916; 382/128, 293, 294, 295; 392/81

(56) References Cited

U.S. PATENT DOCUMENTS

| | | | | |
|---|---|---|---|---|
| 5,615,675 A | * | 4/1997 | O'Donnell et al. | 600/425 |
| 5,924,986 A | * | 7/1999 | Chandler et al. | 600/407 |
| 6,083,168 A | * | 7/2000 | Hossack et al. | 600/443 |
| 6,200,267 B1 | * | 3/2001 | Burke | 600/443 |
| 6,309,352 B1 | * | 10/2001 | Oraevsky et al. | 367/7 |
| 6,352,508 B1 | * | 3/2002 | Pang et al. | 600/443 |

OTHER PUBLICATIONS

T. Motizuki, "A Principle of Three–Dimensional Display", Clinical radiation, vol. 43, No. 11, (1998), pp. 1281–1287 with English translation.

* cited by examiner

Primary Examiner—George Manuel
Assistant Examiner—Ali M. Imam
(74) Attorney, Agent, or Firm—Sughrue Mion, PLLC

(57) ABSTRACT

A method of generating three-dimensional image data by transmitting beams to an object from a transmitting part and detecting beams reflected from the object by using a two-dimensional sensor array having a plurality of sensors. The method includes the steps of: (a) storing detection signals obtained by the plurality of sensors during a predetermined period after transmission; (b) obtaining image data about at least one measured point included in the object on the basis of a detection signal output from at least one of the plurality of sensors at a time point obtained from relationship between a distance from the transmission part to at least one of the plurality of sensors through the at least one measured point and a transmission velocity of the beams passing through the object; and (c) obtaining image data by repeating step (b) while changing the time point.

16 Claims, 8 Drawing Sheets

METHOD OF GENERATING IMAGE DATA AND ULTRASONIC DIAGNOSTIC APPARATUS USING THE SAME

BACKGROUND OF THE INVENTION

1. Field of the Invention

The present invention relates to a method of generating three-dimensional image data on the basis of a plurality of two-dimensional image data that are obtained at different time, and further relates to an ultrasonic diagnostic apparatus for medical diagnosis using the method of generating image data.

2. Description of a Related Art

Conventionally, in order to obtain three-dimensional images using ultrasonic diagnostic apparatus, a plurality of cross-sectional two-dimensional images are collected, and the three-dimensional images are composed thereof. These two-dimensional cross-sectional images are obtained by synthesizing a plurality of picture element data, which were collected in time series by scanning an object by using a one-dimensional sensor array with a positioning sensor, and then, three-dimensional data is obtained by interpolating between cross sections on the basis of a plurality of two-dimensional cross-sectional images.

According to this method, however, there are time lags in the scanning direction of the sensor array, and therefore, cross-sectional images at different time are synthesized. Also, since the images are synthesized on the basis of information obtained by monitoring a position of the sensor, the composite images become unclear. Thus, this method is not suitable for synthesizing images of a living body such as in an ultrasonic diagnostic apparatus.

In order to solve the problem, it is desirable to use a two-dimensional sensor array for obtaining three-dimensional images. For example, it may be considered to collect ultrasonic signals as optical two-dimensional images by using an optical fiber array. According to this method, a plurality of two-dimensional data can be sequentially collected on the basis of ultrasonic signals incident on the two-dimensional sensor array when a predetermined time has passed after an ultrasonic wave is transmitted. However, the two-dimensional data includes all incident ultrasonic signals when the predetermined time has passed after transmitting, and therefore, it would not represent data about a specific point in three-dimensional space if not adjusted.

In the meantime, a document titled "A principle of three-dimensional display" written by Tsuyoshi Mochizuki is reported in "Clinical Radiation" Vol. 43 No. 11 (1998). In this document, it is reported that conventional methods of collecting data by changing sections scanned by ultrasonic waves take a large quantity of time before the whole data aggregate is obtained, and therefore, in the case where a scanned object is a moving one, a precise image cannot be obtained. The document refers to a data collection method using a moving two-dimensional piezoelectric transducer array as one of possible solutions, and also it refers to a method of displaying a surface and internal information of an object simultaneously as a direct method. However, it mentions that hardware and signal processing need a large scale of operation at the present time.

SUMMARY OF THE INVENTION

The present invention has been accomplished in view of such problems as mentioned above. The first object of the present invention is to provide a method of generating three-dimensional images on the basis of a plurality of two-dimensional data obtained at different time by using a two-dimensional sensor array. The second object of the present invention is to provide an ultrasonic diagnostic apparatus using such a method as above.

In order to solve the above problem, a method of generating three-dimensional image data by transmitting beams to an object to be measured by using transmitting means and detecting beams reflected from the object by using a two-dimensional sensor array including a plurality of sensors, according to the present invention comprises the steps of: (a) sequentially storing detection signals obtained by the plurality of sensors during a predetermined period of time after transmission; (b) obtaining image data about at least one measured point included in the object on the basis of a detection signal output from at least one of the plurality of sensors at a time point obtained from relationship between a distance from the transmitting means to at least one of the plurality of sensors through the at least one measured point and a transmission velocity of the beams passing through the object; and (c) obtaining image data by repeating step (b) while changing the time point.

Also, an ultrasonic diagnostic apparatus according to the present invention comprises: a driving signal generating means for generating driving signals; ultrasonic transmitting means for transmitting ultrasonic waves to an object to be measured on the basis of driving signals generated by the driving signal generating means; a two-dimensional sensor array including a plurality of sensors for detecting ultrasonic waves reflected from the object to generate detection signals; signal processing means for processing the detection signals obtained by the plurality of sensors; control means for controlling action timing of the driving signal generating circuit and the signal processing means; storage means for storing the detection signals output from the signal processing means during a predetermined period after transmission; and image processing means for obtaining three-dimensional image data on the basis of the detection signals output from the plurality of sensors at respective time points obtained from relationship between respective distances from the ultrasonic transmitting means to respective sensors through respective measured points and a transmission velocity of the ultrasonic waves passing through the object.

According to the present invention, three-dimensional image data can be generated on the basis of a plurality of two-dimensional image data sequentially obtained at the same sensor position by using a two-dimensional sensor array. Accordingly, clear three-dimensional images can be obtained even in the ultrasonic diagnostic apparatus used for an object of a living body.

DESCRIPTION OF THE PREFERRED EMBODIMENTS

Figure 1:
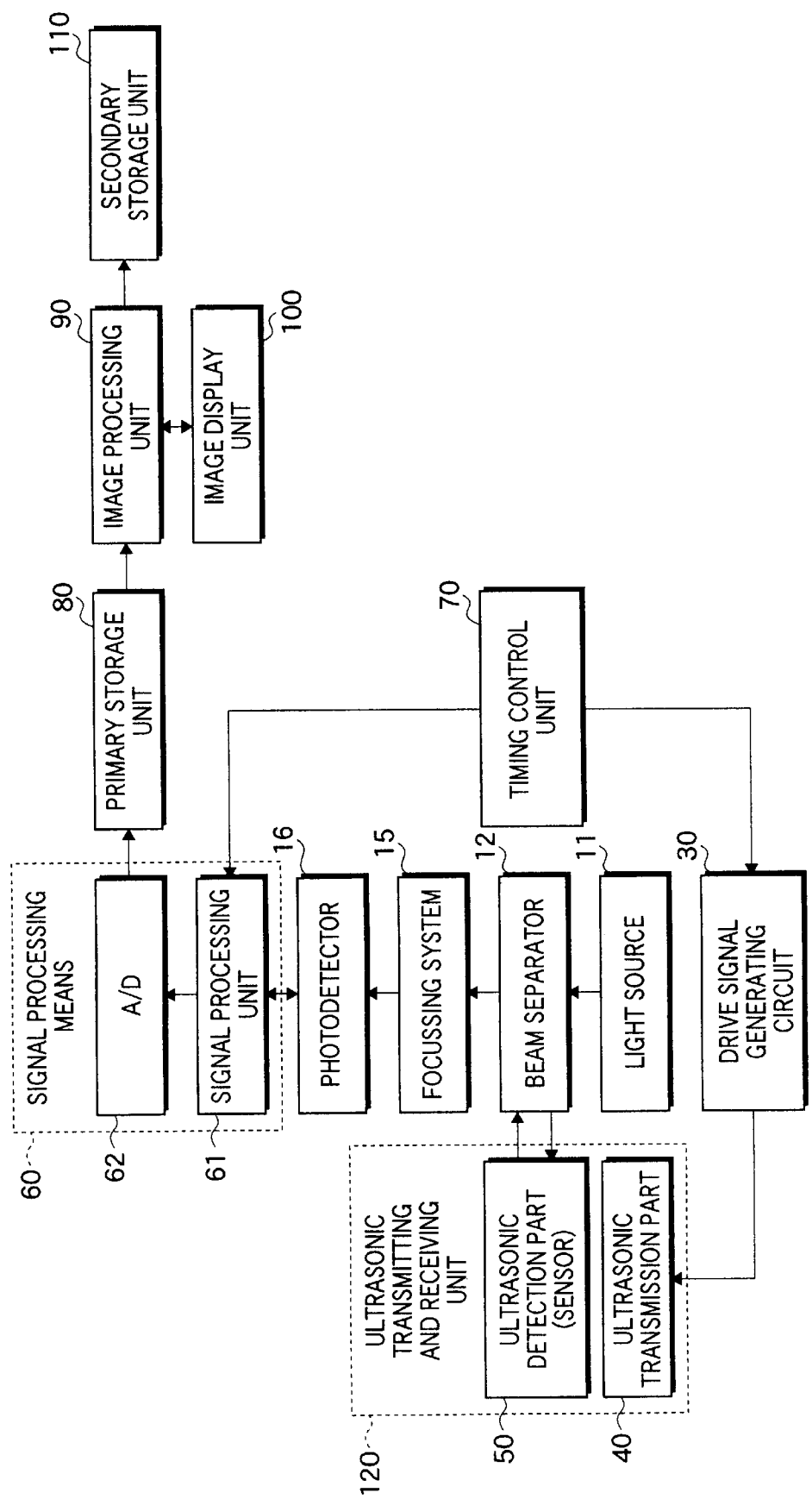
FIG. 1 is a block diagram showing an ultrasonic diagnostic apparatus according to one embodiment of the present invention.

Embodiments of the present invention will be explained in detail with reference to the drawings. The same reference numerals designate the same components throughout the several drawings, and explanation about the same components is omitted.

FIG. 1 is a block diagram showing an ultrasonic diagnostic apparatus according to one embodiment of the present invention. As shown in FIG. 1, the ultrasonic diagnostic apparatus includes a drive signal generating circuit 30 for generating a drive signal and an ultrasonic transmission part 40 for transmitting an ultrasonic wave in accordance with the drive signal. The ultrasonic transmission part 40 includes a piezoelectric transducer using a piezoelectric element, such as PZT (Pb (lead) zirconate titanate) or PVDF (polyvinyl difluoride), or a probe (one-dimensional array) in which piezoelectric transducers are arranged in a line. An ultrasonic wave transmitted to a diagnostic object is reflected from the diagnostic object and received by an ultrasonic detection part (sensor) 50. The sensor 50 includes an optical fiber array, ultrasonic detecting element and so on.

The ultrasonic diagnostic apparatus includes a light source 11, a beam separator 12, a focusing system 15 and a photodetector 16. The detection signal output from the photodetector 16 is input into a signal processing unit 61 included in a signal processing means 60, and furthermore the detection signal is converted to a digital signal in an A/D converter 62 also included in the signal processing means 60.

The A/D converter 62 is connected with a primary storage unit 80, and data of sections of the object are stored in the primary storage unit 80. An image processing unit 90 reconstructs two-dimensional image data or three-dimensional image data on the basis of these data. The method of generating image data in the image processing unit will be explained in detail afterwards. The image processing unit 90 further conducts interpolation, response modulation, gradation process and so on for the reconstructed data and an image display unit 10 displays an image on the basis of the data.

Furthermore, the data processed by the image processing unit 90 is stored in a secondary storage unit 110.

A timing control unit 70 controls the drive signal generating circuit 30 so that drive signals can be generated at predetermined timing, and the timing control unit 70 controls the signal processing unit 61 to catch detection signals output from the photodetector 16 after a predetermined time has passed since the drive signal is transmitted.

Now, four examples will be explained below as the system of the ultrasonic detection part (sensor) 50.

Figure 2:
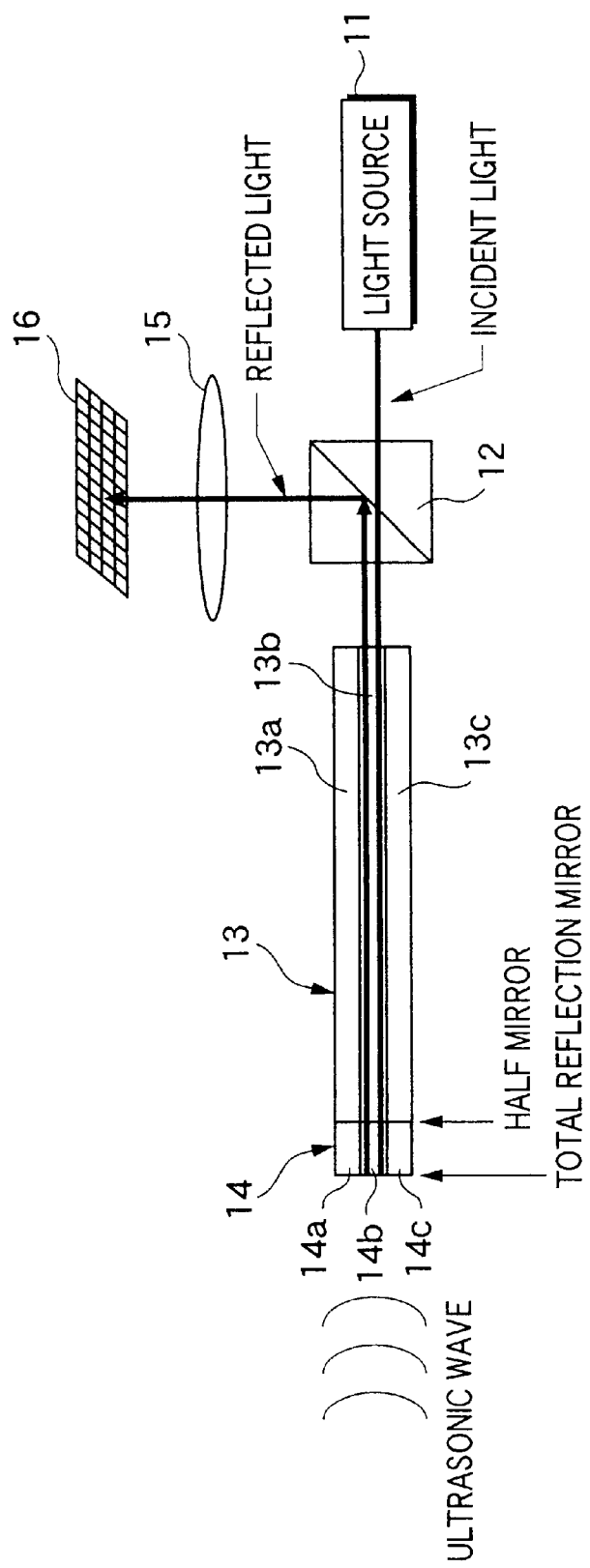
FIG. 2 is a diagram schematically showing a first example of an ultrasonic detection part used for the ultrasonic transmitting and receiving unit as shown in FIG. 1.

(1) An Example Wherein the Optical Fiber Array is Used at the Ultrasonic Detection Part FIG. 2 is a diagram schematically showing an ultrasonic diagnostic detection part including an optical fiber array provided with the ultrasonic detecting elements as a two-dimensional sensor array. As shown in FIG. 2, the optical fiber array 13 includes fine optical fibers 13a, 13b, 13c . . . whose sections are arranged in a two-dimensional matrix form. The ultrasonic detecting element 14 includes, for example, Fabry-Perot resonators (abbreviated as FPR) 14a, 14b, 14c . . . or fiber Bragg gratings (abbreviated as FBG), each formed at the tip of the optical fibers.

Light emitted from the light source 11 passes through the beam separator 12, and then, it is incident on the optical fiber array 13. The light incident on each optical fiber is reflected on a half mirror (on the right end in FIG. 2) and on a total reflection mirror (on the left end in FIG. 2) which are formed on both ends of the FPR. Since a surface of the total reflection mirror is displaced geometrically by the ultrasonic wave transmitted to the ultrasonic detecting elements 14, the reflected light is modulated and again enters the beam separator 12. The reflected light incident on the beam separator 12 is focused on the photodetector 16 directly or through optical fibers, or the focusing system 15 such as a lens or the like.

Figure 3:
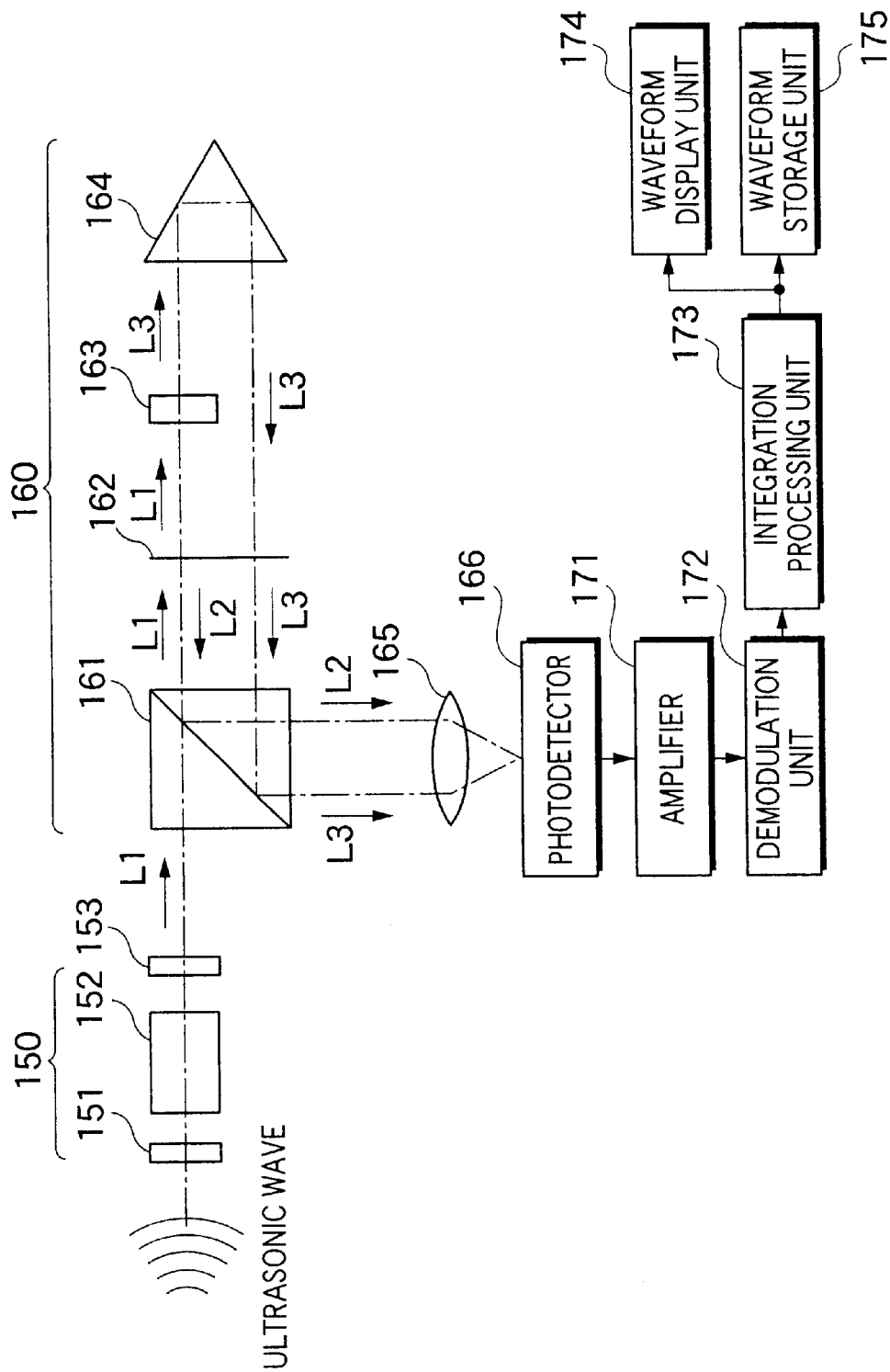
FIG. 3 is a diagram schematically showing a second example of an ultrasonic detection part used for the ultrasonic transmitting and receiving unit as shown in FIG. 1.

(2) An Example Wherein an Optical Heterodyne Interference Optical System is Used for the Ultrasonic Detection Part FIG. 3 is a diagram schematically showing an ultrasonic detection part including a two-dimensional sensor array using an optical heterodyne interference optical system having a difference of optical path lengths. When an ultrasonic wave is incident, a total reflection mirror 151 of a laser resonator 150 is displaced and a distance between the total reflection mirror 151 and a transmission mirror 153 changes. At this time, a frequency of a standing wave, i.e. a resonance frequency produced between the two mirrors installed at both sides of an activated material 152 changes, and an oscillation frequency of laser also deviates. When the laser beams is incident on an interference optical system 160, a difference of optical path lengths is produced between a light beam L2 that transmits through a beam separator 161, reflects on a partial reflection mirror 162 and the beam separator 161 and enters a photodetector 166 through a lens 165 and a light beam L3 that transmits through the partial reflection mirror 162, passes through the frequency shifter 163 and a prism 164, again passes through the partial reflection mirror 162, reflects on the beam separator 161 and enters the photodetector 166 through the lens 165.

Here, when the light beam, whose oscillation frequency deviates as time changes, enters the optical heterodyne interference optical system having the difference of optical path lengths, the beat signals of the frequency are produced whose frequency shifts by the amount of change in the oscillation frequency equivalent to the amount of the delay time around the previous frequency of optical heterodyne interference signals. The frequency-modulated beat signals are amplified by an amplifier 171 and demodulated by a demodulation unit 172, and the obtained demodulation signals are integrated by an integration processing unit 173, so that change in the frequency, i.e. ultrasonic waveforms, can be reproduced. The waveforms are displayed on a waveform display unit 174 and stored in the waveform storage unit 175.

Figure 4:
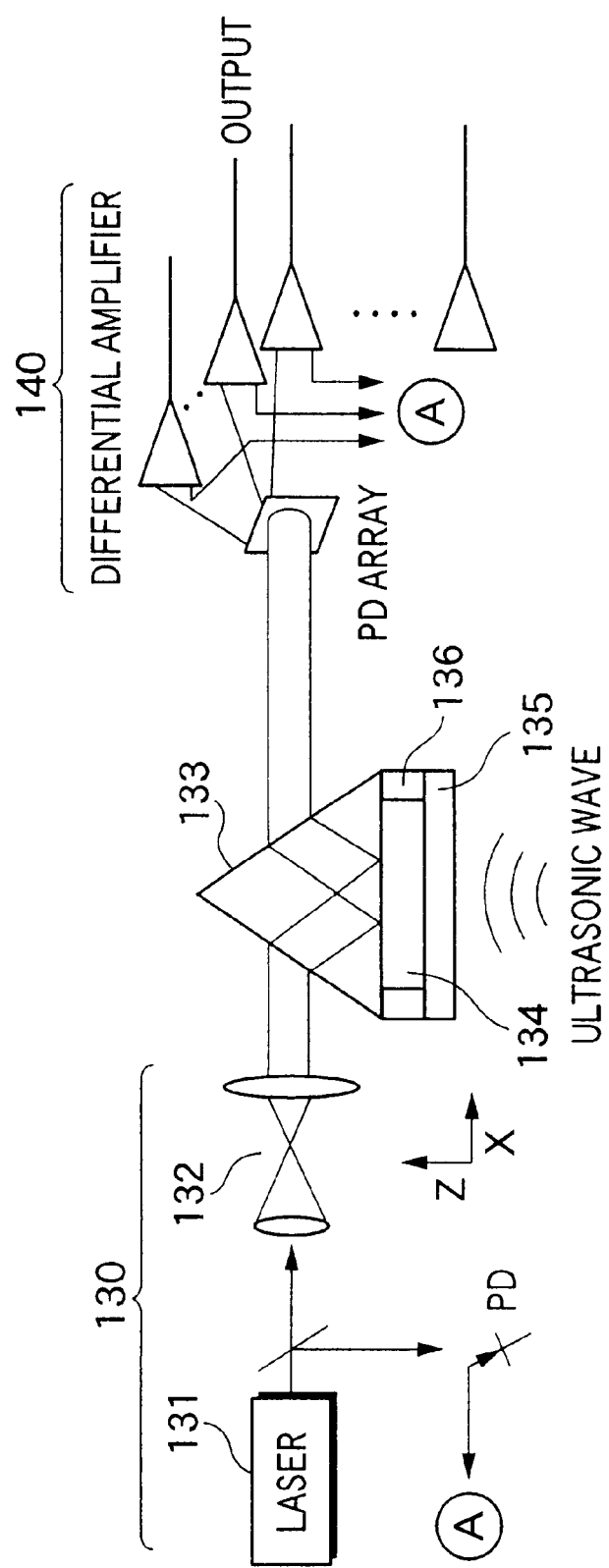
FIG. 4 is a diagram schematically showing a third example of an ultrasonic detection part used for the ultrasonic transmitting and receiving unit as shown in FIG. 1.

(3) An Example Wherein an Evanescent Field is Used for the Ultrasonic Detection Part FIG. 4 is a diagram schematically showing an ultrasonic detection part including an ultrasonic transducer utilizing a fact that quantity of evanescent light varies in accordance with vibration of an object located in an evanescent field near a light reflecting surface owing to reception of ultrasonic waves. As shown in FIG. 4, an ultrasonic transducer includes a prism 133, a gap 134, an optical flat 135 and a spacer 136 for making the gap. When an ultrasonic wave is transmitted into the bottom of the optical flat 135, the quantity of total reflection light at the bottom of the prism 133 varies in accordance with strength of sound pressure of the ultrasonic wave. Accordingly, by irradiating a magnified laser beam emitted from the light source 130, which includes a laser resonator 131 and a beam magnifier 132, to the bottom of the prism 133, and by detecting a strength distribution of the total reflection light by using a photodetector 140, the space distribution and time variation of the ultrasonic wave is measured.

Figure 5:
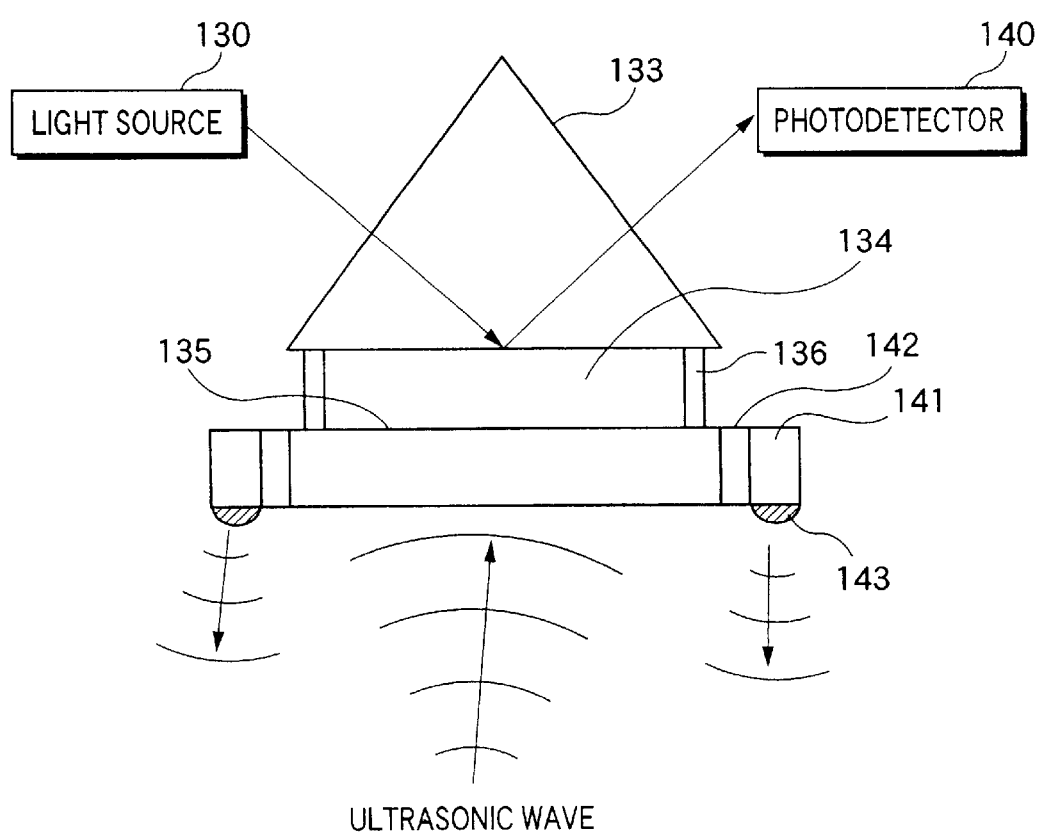
FIG. 5 is a diagram schematically showing a fourth example of an ultrasonic detection part used for the ultrasonic transmitting and receiving unit as shown in FIG. 1.

(4) An Example of Integration of an Ultrasonic Detection Part and an Ultrasonic Transmission Part Since an ultrasonic detection part is not equipped with a function for transmitting ultrasonic waves, one possible solution is to make an ultrasonic transmitting and receiving unit (a probe) 120 by combining an ultrasonic detection part with an ultrasonic transmission part using piezoelectric elements or others. FIG. 5 shows an example of the probe wherein a transmitting function and a receiving function of ultrasonic waves are combined. As shown in FIG. 5, piezoelectric elements (PZT) are installed as an ultrasonic transmission part to the ultrasonic transducer that utilize the fact that quantity of evanescent light varies in accordance with vibration of an object locating in an evanescent field near a light reflecting surface owing to reception of ultrasonic waves. The piezoelectric element (PZT) 141 is installed on the optical flat 135 with an acoustic absorption layer 142 arranged therebetween, and focusing beams are formed by using an acoustic lens 143.

Referring to FIG. 1 again, while the timing control unit 70 outputs fetching signals of data, which detected by the photodetector 16, at the time when a predetermined time has passed after transmission, and then, a signal representing intensity of light which was incident into the photodetector 16 within a predetermined time is input to the signal processing unit 61 as an electric signal, and the intensity signal is sequentially converted into digital signals by an A/D converter 62. By repeating this process while changing startup time of obtaining data and collecting a plurality of data sets, a plurality of two-dimensional data (data of sections) can be obtained.

A plurality of the collected data of sections are stored in the primary storage unit 80, and two-dimensional or three-dimensional data is reconstructed in the image processing unit 90 on the basis of the data. The image processing unit 90 further conducts interpolation, response modulation, gradation process and so on for the reconstructed data, and the image display unit 100 displays images on the basis of the data. Furthermore, the data processed by the image processing unit 90 are stored at the secondary storage unit 110.

The following three kinds of combinations are available for the combination of types of transmission beams from the ultrasonic transmission part 40 and characteristics of detecting elements in the ultrasonic detection part (sensor) 50, and a processing method of the obtained data is changed in accordance with the above combination. It should be noted that these are based on the case where a single element is used for transmitting and a plurality of elements are used for detecting in the followings.

Figure 6:
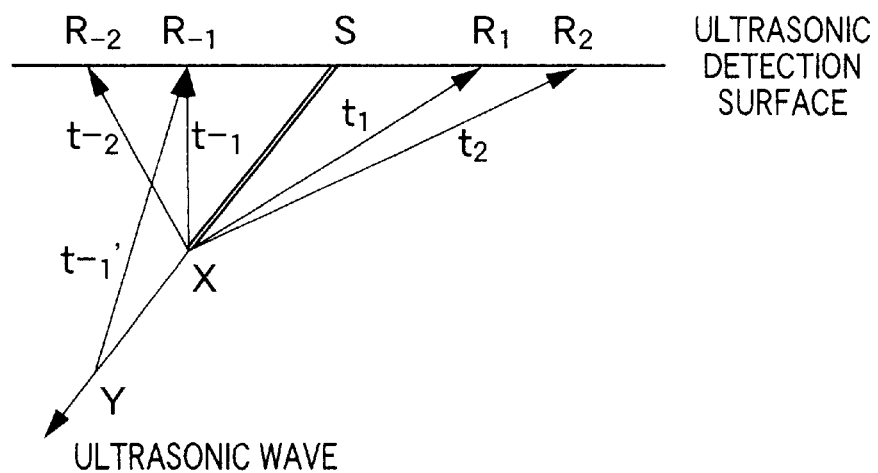
FIG. 6 is a diagram for explaining a method of generating image data according to a first embodiment of the present invention.
Figure 7:
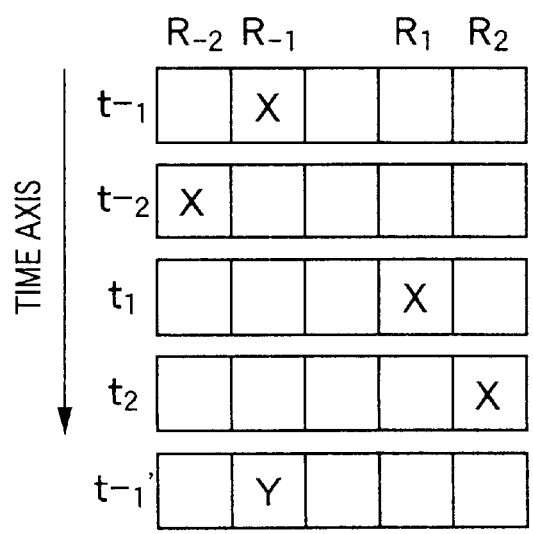
FIG. 7 is a diagram for explaining a method of generating image data according to the first embodiment of the present invention.

FIGS. 6 and 7 are diagrams for explaining a method of generating image data according to a first embodiment of the present invention, wherein transmission beams have directivity and the detecting elements have non-directivity. For example, in the case of collecting the data about point X, transmission beams are transmitted from transmission point S towards point X.

(Distance between $S\text{-}X\text{-}R_{-1}$)/(Velocity of ultrasonic wave) $=t_{-1}$ (1)

(Distance between $S\text{-}X\text{-}R_{-2}$)/(Velocity of ultrasonic wave) $=t_{-2}$ (2)

(Distance between $S\text{-}X\text{-}R_{1}$)/(Velocity of ultrasonic wave) $=t_{1}$ (3)

(Distance between $S\text{-}X\text{-}R_{2}$)/(Velocity of ultrasonic wave) $=t_{2}$ (4)

Where, $R_1$ represents each detecting element. The signal value $R_{-1}(t_{-1})$ of each detecting point at time $t_{-1}$ relates to point X. Similarly, all of the signal value $R_{-2}(t_{-2})$ at time $t_{-2}$, the signal value $R_1(t_1)$ at time $t_1$, and the signal value $R_2(t_2)$ at time $t_2$ are included to a signal $R_x$ relating to point X (See FIG. 7).

Therefore, if they are added as follows:

$$R_x = R_{-1}(t_{-1}) + R_{-2}(t_{-2}) + \ldots + R_1(t_1) + R_2(t_2) + \ldots = \Sigma R_i(t_i) \quad (5)$$

Then, data with high SN ratio can be computed. Alternatively, one element may be used as a representative value without adding. Concerning another point Y, a signal value about the point Y: $R_y = \Sigma R_j(t_j)$ may be computed by adding related data based on the distance between S-Y-each detecting element ($R_j$).

In practice, since relationship between the position of a measuring point and a position of each detecting element R is predetermined, a related expression which represents each signal value $R_i(t_i)$ as a component at the time $t_i$ can be calculated from the relationship and stored in a memory. Also, $\Sigma R_i(t_i)$ maybe used as it is, or the value obtained by compensating quantity of attenuation of ultrasonic waves proportionate to the distance of (sending point S—point X—each receiving point $R_i$) may be used. By obtaining these data through scanning an object with transmission beams two-dimensionally, data of sections can be obtained.

Figure 8:
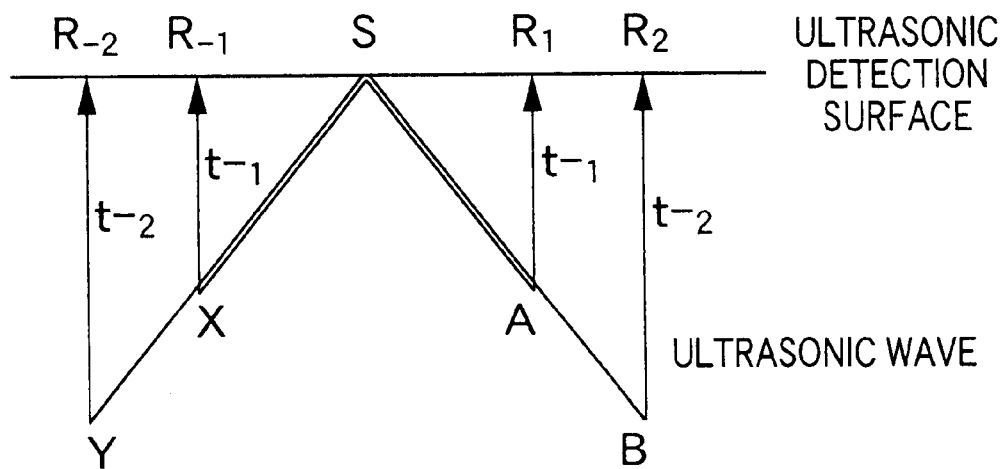
FIG. 8 is a diagram for explaining a method of generating image data according to a second embodiment of the present invention.
Figure 9:
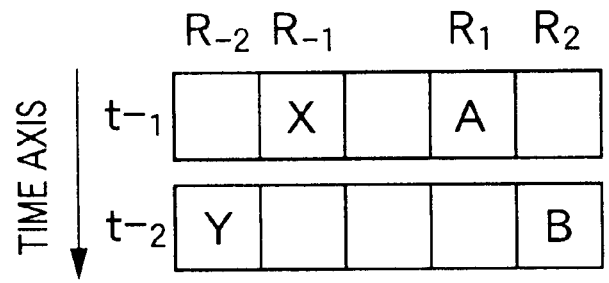
FIG. 9 is a diagram for explaining a method of generating image data according to the second embodiment of the present invention.

Next, referring to FIGS. 8 and 9, a method of generating image data according to a second embodiment of the present invention will be explained. FIGS. 8 and 9 are diagrams for explaining this method. Here, explanation is given in the case where non-directional transmission beams and directional detecting elements are used.

Since the detecting element has directivity, it is assumed that only signals coming from right underneath of the detecting element can be detected. As shown in FIG. 8, by using $t_1$ determined on the basis of the equation (1), the signal value $R_{-1}$ at time $t_{-1}$ represents the signal from point x only. Also, a signal value $R_1$ at the same time $t_{-1}$ represents the signal from point A only. Similarly, the signal values $R_{-2}$ and $R_2$ at the same time $t_{-2}$ represent the signals from point y and point B only. That is, the signals about point X, Y and point A, B are determined without any complications (see FIG. 9), and thus scanning transmission beams is not required any more.

Figure 10:
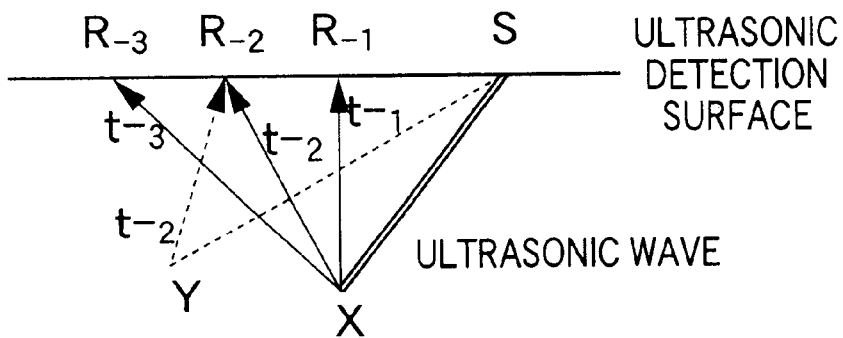
FIG. 10 is a diagram for explaining a method of generating image data according to a third embodiment of the present invention.
Figure 11:
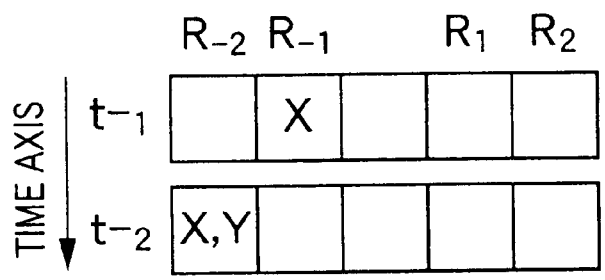
FIG. 11 is a diagram for explaining a method of generating image data according to the third embodiment of the present invention.

In addition, referring to FIGS. 10 and 11, a method of generating image data according to a third embodiment of the present invention will be explained. FIGS. 10 and 11 are diagrams for explaining this method. Here, explanation is given in the case where both transmission beams and detecting elements have non-directivity.

As shown in FIG. 10, for example, a signal value $R_{-2}(t_{-2})$ at time $t_{-2}$ includes signals from point X and Y. Therefore, if adding is done in the same way as the expression (5), data from other points of the same time will be mixed in there as shown in FIG. 11. However, by increasing the components at the time of addition, influence of data from other points may be reduced comparatively. In this case, it is desirable that the data at each receiving point are weighted as required.

As mentioned above, according to the present invention, three-dimensional image data can be generated on the basis of a plurality of two-dimensional image data sequentially obtained at the same array position by using a two-dimensional sensor array. Accordingly, clear three-dimensional images can be obtained in the ultrasonic diagnostic apparatus designed specifically for a living body.

What is claimed is:

1. A method of generating three-dimensional image data by transmitting beams to an object to be measured by using transmitting means and detecting beams reflected from said object by using a two-dimensional sensor array including a plurality of sensors, said method comprising the steps of:
   (a) sequentially storing detection signals obtained by said plurality of sensors during a predetermined period of time after transmission;
   (b) obtaining image data about at least one measured point included in said object on the basis of a detection signal output from at least one of said plurality of sensors at a time point obtained from relationship between a distance from said transmitting means to at least one of said plurality of sensors through the at least one measured point and a transmission velocity of the beams passing through said object; and
   (c) obtaining image data by repeating step (b) while changing said time point.

2. A method of generating three-dimensional image data by transmitting directional beams to said object and detecting beams reflected from said object by using a two-dimensional sensor array including a plurality of non-directional sensors, according to claim 1, wherein:
   step (b) includes obtaining image data about at least one measured point included in said object on the basis of a detection signal output from the at least one of said plurality of sensors at least one time point obtained from relationship between a distance from said transmitting means to at least one of said plurality of sensors through the at least one measured point and the transmission velocity of the beams passing through said object;
   step (c) includes obtaining image data about a plurality of measured points on the linear transmission beams by repeating step (b) while changing said at least one time point; and
   said method further comprises step (d) of obtaining three-dimensional image data by repeating steps (a) through (c) while scanning said object with transmission beams two-dimensionally.

3. A method according to claim 2, wherein step (b) includes obtaining image data by adding detection signals about one measured point out of detection signals sequentially output from said plurality of sensors.

4. A method of generating three-dimensional image data by transmitting non-directional beams to said object and detecting beams reflected from said object by using a two-dimensional sensor array including a plurality of directional sensors, according to claim 1, wherein:
   step (b) includes obtaining image data about a plurality of measured points included in said object on the basis of a plurality of detection signals output from selected sensors at respective time points obtained from relationship between the distances from said transmitting means to respective sensors through respective measured points and the transmission velocity of the beams passing through said object; and
   step (c) includes obtaining three-dimensional image data by repeating step (b) while changing said time points.

5. A method of generating three-dimensional image data by transmitting non-directional beams to said object and detecting beams reflected from said object by using a two-dimensional sensor array including a plurality of non-directional sensors, according to claim 1, wherein:
   step (b) includes obtaining image data about a plurality of measured points included in said object on the basis of detection signals output from said plurality of sensors at respective time points obtained from relationship between distances from said transmitting means to respective sensors through respective measured points and the transmission velocity of the beams passing through said object; and
   step (c) includes obtaining three-dimensional image data by repeating step (b) while changing said time points.

6. A method according to claim 5, wherein step (b) includes obtaining image data by weighting a detection signal about one measured point out of detection signals sequentially output from said plurality of sensors.

7. An ultrasonic diagnostic apparatus comprising:
   driving signal generating means for generating driving signals;
   ultrasonic transmitting means for transmitting ultrasonic waves to an object to be measured on the basis of driving signals generated by said driving signal generating means;
   a two-dimensional sensor array including a plurality of sensors for detecting ultrasonic waves reflected from said object to generate detection signals;
   signal processing means for processing the detection signals obtained by said plurality of sensors;
   control means for controlling action timing of said driving signal generating circuit and said signal processing means;
   storage means for storing the detection signals output from said signal processing means during a predetermined period after transmission; and
   image processing means for obtaining three-dimensional image data on the basis of the detection signals output from said plurality of sensors at respective time points obtained from relationship between respective distances from said ultrasonic transmitting means to respective sensors through respective measured points and a transmission velocity of the ultrasonic waves passing through said object.

8. An ultrasonic diagnostic apparatus according to claim 7, wherein:
   said ultrasonic transmitting means transmits directional ultrasonic waves toward said object;
   said two-dimensional sensor array includes a plurality of non-directional sensors; and
   said image processing means obtains image data about one measured point on the basis of detection signals output from at least one sensor out of said plurality of sensors at least one time point obtained from relationship between a distance from said ultrasonic transmitting means to at least one of said plurality of sensors through one measured point and the transmission velocity of the ultrasonic waves passing through said object, obtains image data about a plurality of measured points included in said object while changing said at least one time point and obtains three-dimensional image data by repeating above operation while scanning said object with transmission ultrasonic waves two-dimensionally.

9. An ultrasonic diagnostic apparatus according to claim 8, wherein said image processing means obtains image data by adding detection signals about one measured point out of detection signals sequentially output from said plurality of sensors.

10. An ultrasonic diagnostic apparatus according to claim 7, wherein:

said ultrasonic transmitting means transmits non-directional ultrasonic waves toward said object;

said two-dimensional sensor array includes a plurality of directional sensors; and said image processing means obtains image data about a plurality of measured points included in said object on the basis of a plurality of detection signals output from respective sensors at respective time points obtained from relationship between distances from said ultrasonic transmitting means to respective sensors through respective measured points and the transmission velocity of the ultrasonic waves passing through said object, and obtains three-dimensional image data by repeating above operation while changing said time points.

11. An ultrasonic diagnostic apparatus according to claim 7, wherein:

said ultrasonic transmitting means transmits non-directional ultrasonic waves toward said object;

said two-dimensional sensor array includes a plurality of non-directional sensors; and said image processing means obtains image data about a plurality of measured points included in said object on the basis of detection signals output from said plurality of sensors at respective time points obtained from relationship between distances from said ultrasonic transmitting means to respective sensors through respective measured points and the transmission velocity of the ultrasonic waves passing through said object, and obtains three-dimensional image data by repeating above operation while changing said time points.

12. An ultrasonic diagnostic apparatus according to claim 11, wherein said image processing means obtains image data by weighting a signal relating to one measured point out of detection signals sequentially output from said plurality of sensors.

13. An ultrasonic diagnostic apparatus according to claim 7, wherein said two-dimensional sensor array includes an optical fiber array having an ultrasonic sensing part for detection of ultrasonic waves.

14. An ultrasonic diagnostic apparatus according to claim 7, wherein said two-dimensional sensor array includes a laser resonator that changes an emission frequency by receiving ultrasonic waves and enters emission light into an optical heterodyne interference optical system.

15. An ultrasonic diagnostic apparatus according to claim 7, wherein said two-dimensional sensor array includes a sensor for detecting ultrasonic waves by utilizing the fact that an object locating in an evanescent field near a light reflecting surface vibrating by receiving ultrasonic waves causes change in a quantity of reflected/transmitted light at said light reflecting surface.

16. An ultrasonic diagnostic apparatus according to claim 7, wherein a probe includes said ultrasonic transmitting means and said two-dimensional sensor array having ultrasonic conversion systems different from each other.

* * * * *